(12) United States Patent
Malanoski et al.

(10) Patent No.: US 7,979,446 B2
(45) Date of Patent: Jul. 12, 2011

(54) COMPUTER-IMPLEMENTED BIOLOGICAL SEQUENCE IDENTIFIER SYSTEM AND METHOD

(75) Inventors: Anthony P. Malanoski, Washington, DC (US); Baochuan Lin, Bethesda, MD (US); Joel M Schnur, Burke, VA (US); David A Stenger, Herndon, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/617,025

(22) Filed: Nov. 12, 2009

(65) Prior Publication Data
US 2010/0070195 A1    Mar. 18, 2010

Related U.S. Application Data (60) Division of application No. 11/422,431, filed on Jun. 6, 2006, now Pat. No. 7,623,997, which is a continuation-in-part of application No. 11/177,646, filed on Jul. 2, 2005, now abandoned, and a continuation-in-part of application No. 11/177,647, filed on Jul. 2, 2005, and a continuation-in-part of application No. 11/268,373, filed on Nov. 7, 2005, now abandoned.

(60) Provisional application No. 60/590,931, filed on Jul. 2, 2004, provisional application No. 60/609,918, filed on Sep. 15, 2004, provisional application No. 60/631,460, filed on Nov. 29, 2004, provisional application No. 60/631,437, filed on Nov. 29, 2004, provisional application No. 60/691,768, filed on Jun. 16, 2005, provisional application No. 60/626,500, filed on Nov. 5, 2004, provisional application No. 60/735,876, filed on Nov. 14, 2005, provisional application No. 60/735,824, filed on Nov. 14, 2005, provisional application No. 60/743,639, filed on Mar. 22, 2006.

(51) Int. Cl.
*G06F 7/00* (2006.01)
*G06F 17/30* (2006.01)
(52) U.S. Cl. .............. 707/749; 702/20; 703/2; 703/11; 706/48; 707/706; 707/723; 707/776
(58) Field of Classification Search .................. None
See application file for complete search history.

(56) References Cited

U.S. PATENT DOCUMENTS
2002/0015955 A1* 2/2002 Meyerson ............... 435/6

OTHER PUBLICATIONS

Examination report in NZ564992.
Office Action in KR Appl No. 10-2008-7001309.
Written Opinion in SG200718668-7 (Feb. 25, 2010).
Office Action in JP2008-516959 (Dec. 14, 2010).
Goto et al., "Accurate and Rapid Identification Technique for Microorganisms by Homology Search" Fragrance Journal C, 31(3), 62-71 (2003) (Japanese), English abstract only.
Goto et al., "Accurate and Rapid Identification Technique for Microorganisms by Homology Search" Fragrance Journal C, 31(3), 62-71 (2003) (Partial translation).

* cited by examiner

*Primary Examiner* — Carolyn L. Smith
(74) *Attorney, Agent, or Firm* — Amy L. Ressing; Joseph T. Grunkemeyer (57) ABSTRACT

A method of: submitting reference sequences to a taxonomic database to produce taxonomic results; and reporting a taxonomic identification based on the taxonomic results. The reference sequences are the output of genetic database queries that return a score for each reference sequence. A method for processing a biological sequence obtained from an assay by: converting base calls located in a predetermined list of positions within the biological sequence to N; and determining the ratio of single nucleotide polymorphisms in the biological sequence relative to a reference sequence. Each entry in the predetermined list of positions represents the capability of a substance hybridizing to a microarray used to generate the biological sequence. The substance is not the nucleic acid of a target pathogen.

5 Claims, 4 Drawing Sheets

```
                        *****                                                          ***
    FluANA1_Tile  CTGGGTAAATCAAACATATGTCAATATTAACAACACTAACGTTGTTGCTGGAAAGGACACA 184
       A/Weiss/43  CTGGGTAAATCAAACATATGTTAATATTAGCAACACTAACGTTGTTGCTGGAAAAGGCACA 179
 A/PuertoRico/8/34  CTGGGTAAA---------------------------------------------GGACACA 199
       Sample_Raw  CTGGGNNNNNNNNNNNNNNNNNNNNNNNNNNNNNNNNNNNNNGNCGTTGTTGCTGGAAAGGNCACA 184
  Sample_filtered  CTGGGNNNNNNNNNNNNNNNNNNNNNNNNNNNNNNNNNNNNNNNNNNNNNNNNNNNNNNNNNNACA 184
```

Fig. 5

COMPUTER-IMPLEMENTED BIOLOGICAL SEQUENCE IDENTIFIER SYSTEM AND METHOD

This application is a divisional application of U.S. patent application Ser. No. 11/422,431, filed on Jun. 6, 2006, which claims priority to U.S. Provisional Patent Application Nos. 60/691,768, filed on Jun. 16, 2005; 60/735,876 filed on Nov. 14, 2005; 60/735,824 filed on Nov. 14, 2005; and 60/743,639, filed on Mar. 22, 2006, all incorporated herein by reference. U.S. patent application Ser. No. 11/422,431 is a continuation-in-part application of U.S. patent application Ser. Nos. 11/177,647, filed Jul. 2, 2005; 11/177,646, filed Jul. 2, 2005; and 11/268,373, filed on Nov. 7, 2005, all incorporated herein by reference. These nonprovisional applications claim priority to U.S. Provisional Patent Application Nos. 60/590,931, filed on Jul. 2, 2004; 60/609,918, filed on Sep. 15, 2004; 60/626,500, filed on Nov. 5, 2004; 60/631,437, filed on Nov. 29, 2004; and 60/631,460, filed on Nov. 29, 2004, all incorporated herein by reference. U.S. patent application Ser. No. 11/422,425 is incorporated herein by reference. The Sequence Listing filed electronically is incorporated by reference. This application includes a computer program listing appendix filed electronically as a text file. The computer program listing appendix is incorporated herein by reference.

FIELD OF THE INVENTION

The invention is generally related to processing of biological sequences.

DESCRIPTION OF RELATED ART

For both surveillance and diagnostic applications, fine-scale pathogen identification and near-neighbor discrimination is important; therefore, an assay that monitors at this very specific level is desirable in clinical environments (1-3). (All referenced publications and patent documents are incorporated herein by reference.) To successfully use any method based on DNA or RNA detection, these assays must be coupled with large databases of nucleic acid sequence information for assay design to ensure that the desired information is provided and for the interpretation of raw data. Several well established techniques, such as real time PCR, use short, unique stretches of sequenced genomes to provide good specificity (4). These techniques are capable of providing fine-scale identification of several genetically close organisms by selecting a sufficient number of segments. However, these selected segments, which in the initial selection process were specific, are often later found to be less specific as more organisms are sequenced. This is particularly a problem for pathogens belonging to a family with high mutation rate and also for pathogens that have relatively few neighboring pathogens identified. In addition, real time PCR is not capable of detecting the presence of new significant mutations nor can it resolve base sequence details. Similarly, advances in other detection techniques have provided methods of obtaining pathogen identification but suffer from some or all of the problems of using PCR (5-8).

High density resequencing microarrays can produce variable length segments, $10^2$-$10^5$ base pairs (bp), of direct sequence information. They have been successfully used to detect single nucleotide polymorphism (SNP) and genetic variants from viral, bacterial, and eukaryotic genomes (9-16). Their use for SNP detection has clearly established their ability to provide reliable quality sequence information. In most cases, the microarrays were designed to study a limited number of genetically similar target pathogens, and for many cases, the detection methods relied only on recognizing hybridization patterns for identification (12, 14, 15, 17, 18). Taking advantage of sequential base resolution capability of resequencing microarrays that was required for SNP detection, resequencing has recently been successfully adapted using a different approach for pathogen identification of multiple bacterial and viral pathogens while allowing for fine detailed discrimination of closely related pathogens and tracking mutations within the targeted pathogen (19-21). The new methodology differed from earlier work by using the resolved bases as the query of a similarity search of DNA databases to identify the most likely species and variants that match the base calls from the hybridization observed. The system was capable of testing for 26 pathogens simultaneously and could detect the presence of multiple pathogens. A software program, REsequencing Pathogen Identifier (REPI), was used to simplify data analysis by performing similarity searches of a genetic database using Basic Local Alignment Search Tool (BLAST) (22). The REPI program used BLAST default settings and would only return sequences that might represent the hybridization if the expect value, a quantity calculated by the BLAST program that indicates the likelihood that the sequence match found would have occurred by random chance in the database, was less than $10^{-9}$. This screened out all cases that had insufficient signal; however, the final determination of what pathogen(s) was detected and to what degree discrimination was possible required manual examination of the returned results. This method successfully allowed fine discrimination of various adenoviruses and strain identifications of Flu A and B samples in agreement with conventional sampling results (19,20). Two important advantages of this approach were that the information was always recovered at the most detailed level possible and that it was capable of still recognizing organisms with recent mutations. This approach also maintained specificity well, as it was not dependent on the uniqueness of short sequences, which are constantly encroached upon as more organisms are sequenced.

Although this analysis method has utility, there are several shortcomings: it is time consuming, not optimized to maximize sensitivity, has complicated results, is suitable only for an expert, and contains redundant or duplicate information. The process was time consuming because only the initial screening was handled automatically while the remaining steps required manual interpretation before the detection analysis was complete. Because a simple criterion (expect value cutoff of $10^{-9}$) and non-optimized BLAST parameters were used to consider a pathogen detected, the REPI algorithm provided a list of candidate organisms but did not make a final simple conclusion nor could it relate the results of one prototype sequence to another. Instead, a manual process was used to make the final determination, but because the REPI program provided all similar results and the use of public nucleic acid databases containing redundant entries, a large amount of data was presented to a user that was not useful. In addition, with a manual process it was not possible to establish that the algorithm developed was generally applicable for any organism where nucleic acid base resolved sequence information has been provided.

SUMMARY OF THE INVENTION

One method of the invention comprises: submitting a plurality of reference sequences in queries to a taxonomic database to produce a plurality of taxonomic results; and reporting a taxonomic identification based on the taxonomic results.

The reference sequences are the output of genetic database queries that return a score for each reference sequence.

Another method of the invention for processing a biological sequence obtained from an assay comprises: converting base calls located in a predetermined list of positions within the biological sequence to N; and determining the ratio of single nucleotide polymorphisms in the biological sequence relative to a reference sequence. Each entry in the predetermined list of positions represents the capability of a substance hybridizing to a microarray used to generate the biological sequence. The substance is not the nucleic acid of a target pathogen.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

As used herein, the term "sequence" refers to a nucleic acid sequence, such as DNA or RNA, or a protein sequence. As used herein, "base" and "base call" can refer to either nucleotide bases or amino acids. As used herein the term "taxonomic" can refer to any level or class of identification of a pathogen, including but not limited to, genus, species, strain, and substrain. As used herein the term "reporting" can include transmitting a signal from one system to another and producing a human-readable report of any form. All disclosed methods may be computer-implemented on apparatus having the means for performing the methods.

Disclosed is a new software expert system, Computer-Implemented Biological Sequence Identifier system 2.0 (CIBSI 2.0), that can successfully use resolved base sequence information from custom designed Affymetrix resequencing microarrays to provide a simple list of organisms that are detected. This algorithm addresses a shortcoming of previous methods by incorporating new features to completely automate pathogen identification. The single program is capable of making correct decisions for all 26 pathogens contained on the RPM v1 microarray (19, 20, 23), whether detected alone or in combinations, with improved sensitivity. Although the program is currently applied to resequencing microarrays, the methodologies developed remain generally applicable as only the first portion of the algorithm handles issues specific to microarrays while the remainder deals with sequences that are suitable for use as a query by the BLAST algorithm. In developing the general identification algorithm, issues specific to resequencing microarrays that complicate their use were identified and resolved. Because the entire decision process for what is detected has been automated, it is straightforward to test whether the rules used to make identifications are rigorous and applicable to any pathogen. With this efficient program, resequencing based assays can provide a competitive method to test simultaneously for many possible pathogens, providing output that can be interpreted by a non-expert.

The prior art shows that although genetic sequence information can be compared to the contents of a reference genetic database and used to identify a set of possible organisms, further conclusions cannot easily be made. To extend this approach and make it possible to automate the decision, more is needed to simplify the initial results. The solution put forth by this work is to use information (from a taxonomic database) to relate returned queries to each other. This makes it possible to reduce the complexity of the returns and to implement an automated identification process. Automation would not be possible without the ability to relate returns to each other. Utilizing taxonomy simplifies that and leverages work that has already been performed. Furthermore, the taxonomic database makes it possible to compare results from disparate targets and relate them to each other. This is also required to make automation possible and the end result simple to understand. Furthermore, changes were made to the filtering and parsing routines. This allowed for the explicit accounting of issues that arise from using resequencing arrays that otherwise could cause misidentifications.

Amplification, Hybridization, and Sequencing Determination

The details of the RPM v1 microarray design and the experimental methods have been discussed in previous work (19, 20, 23). The experimental microarray data used in the present analysis were obtained using a variety of purified templates and clinical samples using random and multiplexed amplification schemes. GCOS software v1.3 (Affymetrix Inc., Santa Clara, Calif.) was used to align and scan hybridized microarrays to determine the intensity of each probe in every probe set. Base calls were made based on the intensity data of each probe set using GDAS v3.0.2.8 software (Affymetrix Inc., Santa Clara, Calif.) which used an implementation of the ABACUS algorithm (11). The sequences were represented in FASTA format for later analysis steps.

A resequencing microarray (RPM v.1) was previously designed for detection and sequence typing of 20 common respiratory and 6 CDC category A biothreat pathogens known to cause febrile respiratory illness based on ProSeqs without relying on predetermined hybridization patterns (19, 20, 23). Approximately 4000 RPM v.1 experiments, performed using different amplification schemes, single and multiple pathogen targets, purified nucleic acids and clinical samples, were examined in order to develop the pathogen identification algorithm. Results using this algorithm with clinical samples, identified pathogens and purified nucleic acids are discussed in detail in other work (19, 20, 23). In all cases, the algorithm correctly identified the organism at a species or strain level, depending on the length of the ProSeqs represented on the RPM v.1. Some specific examples will be discussed to illustrate how the algorithm performs under a variety of conditions.

Figure 1:
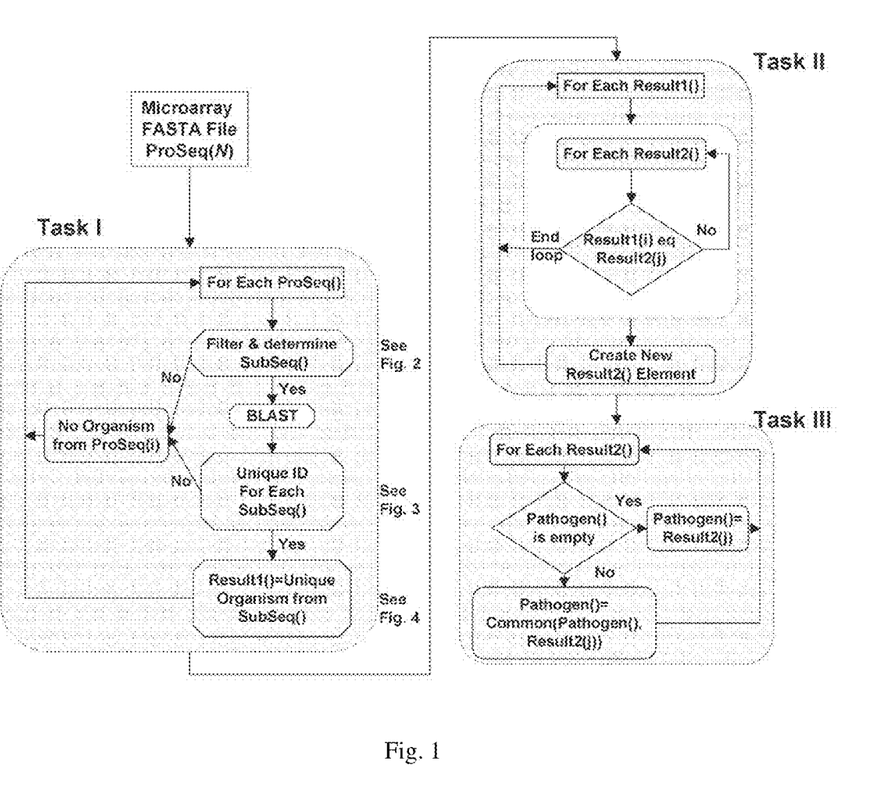
FIG. 1 is a schematic of an algorithm representing the relationship of three main tasks and logic of subtasks associated with tasks. Task I carries out filtering and subsequence selection, and then determines what database records prototype sequences are most similar to. Task II figures whether prototype sequence identifications support a common organism identification. Task III does final examination and decisions of the detected organism from the microarray data. ProSeq: prototype sequence; SubSeq: subsequences; HybSeq: hybridized sequence.

The CIBSI 2.0 program handled a hierarchy of three tasks (FIG. 1): (I) determine to which database records the detected organisms are most similar to, (II) determinate whether the identifications from separate targets support a common organism identification, and (III) determinate whether detected organisms belong to the target set that the assay was designed to detect or are related to close genetic near neighbors. Target pathogens are the organisms the assay was specifically designed to detect. As used herein, the sets of probes that represent reference sequence selected from target pathogen genomes are referred to as a Prototype Sequence or "ProSeq" for brevity. The set of resolved bases that result from hybridization of genomic material to a ProSeq is referred to as the hybridized sequence or "HybSeq". The HybSeq is split into possible subsequences or "SubSeqs". One portion of the algorithm deals with ProSeq-based organism identification and is handled in three steps: initial filtering of individual HybSeqs into SubSeqs suitable for sequence similarity comparisons, database querying of individual SubSeqs, and taxonomic comparison of BLAST returns for each SubSeq. At the next level, ProSeqs were compared to determine if they supported the same identified organism. In the final step, detected organisms were compared to the list of target pathogens the assay was designed for in order to determine if any were positively detected. The level of discrimination that a particular sample supported was automatically determined.

Filtering

Figure 2:
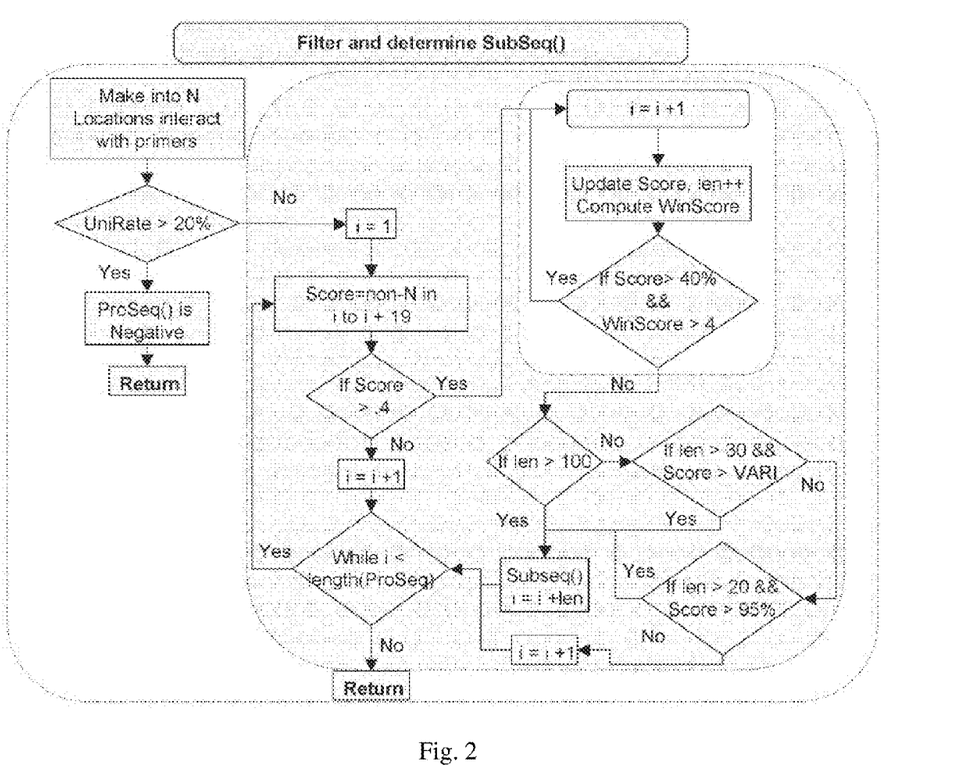
FIG. 2 is a detailed schematic of the filtering subtask of Task 1. For each ProSeq, primers region were masked as N (ambiguous) calls, then UniRate, was calculated from the HybSeq. For ProSeqs which passed the UniRate requirement, a revised sliding window algorithm attempted to grow a SubSeq that could be used as a query to BLAST. The identity (start location in the ProSeq and length) of a successfully grown SubSeq was placed in a file for batch querying via BLAST.

An initial filtering algorithm, REsequencing Pathogen Identifier (REPI), was developed previously (20) and the general concepts with revisions were incorporated into the current (automated detection) algorithm used in the CIBSI 2.0 program. Filtering and subsequence selection were used to remove potential biasing caused by reference sequence choice, and by other sources (primers) as well as separate a HybSeq into fragments of significance for faster searching. This was the first subtask of Task I in FIG. 1 and is shown schematically in detail in FIG. 2. When PCR amplification was used, microarrays were hybridized in the presence of only primers to determine locations where they resulted in hybridization. Any portions of the ProSeqs that hybridized with the primers were masked as N calls so that the HybSeq did not contain biased information. For each ProSeq, the ratio of SNPs to the total number of unique base calls, UniRate, was calculated from the HybSeq. To eliminate HybSeqs with insufficient hybridization if the UniRate was $\geqq 20\%$ (the SNP threshold), the ProSeq was considered negative for target organism detection. A UniRate of 20% indicated that on average there were 5 SNP per 25 bp. It is unrealistic to expect significant specific hybridization of 25 bp probes with this frequency of differences between an organism similar to the target pathogen and the reference sequence that the ProSeq is based on. This would end the filtering subtask and return to the Task I loop, which would examine the next ProSeq. For ProSeqs with a ratio <20%, a more detailed examination was performed. At each location of the HybSeq, a revised sliding window algorithm (20) attempted to grow a SubSeq that could be used as a query to BLAST. Initially, the first 20 bases (initial length) after a location were examined. If less than 60% of those bases were ambiguous, N, the SubSeq entered the extension stage. The SubSeq was extended one base at a time until the total content of unique base calls fell below 40% (unique-base threshold) or if a sliding window containing the last 21 bases had fewer than 4 unique base calls. This was different from the REPI algorithm in which only the sliding window of 20 bases was used and growth of a SubSeq stopped when less than 40% of the windows content was unique base calls. At this point, the SubSeq was examined and trailing N calls were removed. At least one location having 7 contiguous unique base calls was required to meet the word size parameter of BLAST and to keep the SubSeq for further analysis. SubSeqs longer than 100 bases were accepted. For acceptance, SubSeqs$\leqq 30$ bases required at least 95% unique base calls (not "N"). For SubSeqs with 30 to 100 bases, subsequence acceptance required at least VARI (("SubSeq length"$-30)*0.2857+70$) % unique bases. For SubSeqs$\geqq 80$ bases, The BLAST word size parameter was changed to 11 if it contained at least 11 contiguous bases. The identity (start location in the ProSeq and length) of a successfully grown SubSeq was placed in an entry in the SubSeq array that retained information associated with each SubSeq. This identity and the SubSeq were placed in a file for batch querying via BLAST. This procedure was repeated, by continuing from the end of the previous successful SubSeq, or in the case of failure, by continuing from the point the window was initially grown from until the end of the HybSeq. Upon completion, the algorithm returned to the Task I loop and performed the BLAST subtask.

Database Query

Figure 3:
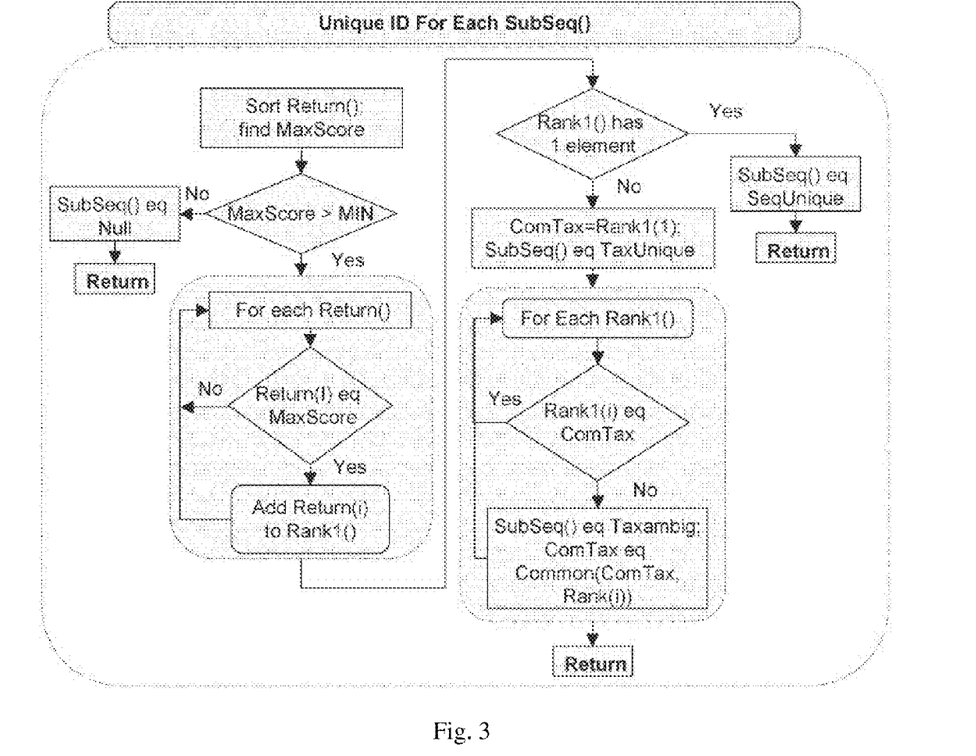
FIG. 3 is a detailed schematic of the subtask of Task 1 responsible for organism identification for an individual SubSeq. Each SubSeq sent to BLAST returned a list of possible matches contained in a Return array that was sorted through to find best bit score/expect value pair (MaxScore). If the MaxScore was greater than MIN ($10^{-6}$), all returns that had this best Score were sorted into a new array Rank1. The detailed decision process described in the method section then the organism of the SubSeq was identified.

The BLAST subtask performed a batch similarity search of a database using SubSeq as the queries. The BLAST program used was the NCBI Blastall -p blastn version 2.12 with a defined set of parameters. The masking of low complex regions was performed for the seeding phase to speed up the query; however, low complexity repeats were included in the actual scoring. The entire nucleotide database from NCBI acquired on Feb. 7, 2006 was used as the reference database. (Note that earlier images of the database were used during development but all experiments were rerun with the algorithm as described with the image of the database obtained on this date.) The default gap penalty and nucleotide match score were used. The nucleotide mismatch penalty, -q, parameter was set to -1 rather than the default. The results of any BLAST query with an expect value<0.0001 were returned in tabular format from the blastall program. The information about each return (bit score, expect value, mismatches, length of match) was placed in the Return{hash key} {info} hash using the SubSeq identity as the hash key for further analysis.
Taxonomy-Base Pathogen Identification for ProSeqs from SubSeqs The next subtask of Task I carried out was the determination of SubSeq( ) states and is shown in FIG. 3. In order to present simple data and to ease the decision process, the information about every SubSeq was summarized by two parameters. The "identified organism" represented the taxonomic class of the organism and the "organism uniqueness" indicated the quality of the organism identification. The elements in the Return hash were examined and ranked by score array for each separate SubSeq( ) of a ProSeq. The Score array contained a pair of parameters, the bit score and the expect value, that had a fixed relationship for a given database. It was sometimes appropriate to use a ranking score that either accounted for the size of the database (expect value) or not (bit score). Elements in the Return hash could have the same scores so all the elements with the highest bit score/lowest expect value (MaxScore) were retained in a separate array Rank1. The full taxonomic classifications of every element in Rank1 were retrieved from the NCBI taxonomy database also obtained on Feb. 7, 2006 (See earlier note). If MaxScore expect values were greater than MAX (currently $10^{-6}$), the SubSeq( ) had its identified organism and organism uniqueness information both updated to null. When MaxScore was sufficiently small, the returns placed in Rank1 were examined. When Rank1 contained a single element, the SubSeq was assigned an organism uniqueness of SeqUniqu. When Rank1 contained multiple elements, the SubSeq was assigned an organism uniqueness of TaxUnique if all returns belonged to the same taxonomy class; otherwise, the SubSeq's organism state was set to TaxAmbig. The tasks outlined in FIG. 3 were applied to each SubSeq( ) of the ProSeq. In all cases, an identified organism was assigned to each SubSeq( ) which represented the taxonomic class that was the common parent of all the elements within Rank1.

Figure 4:
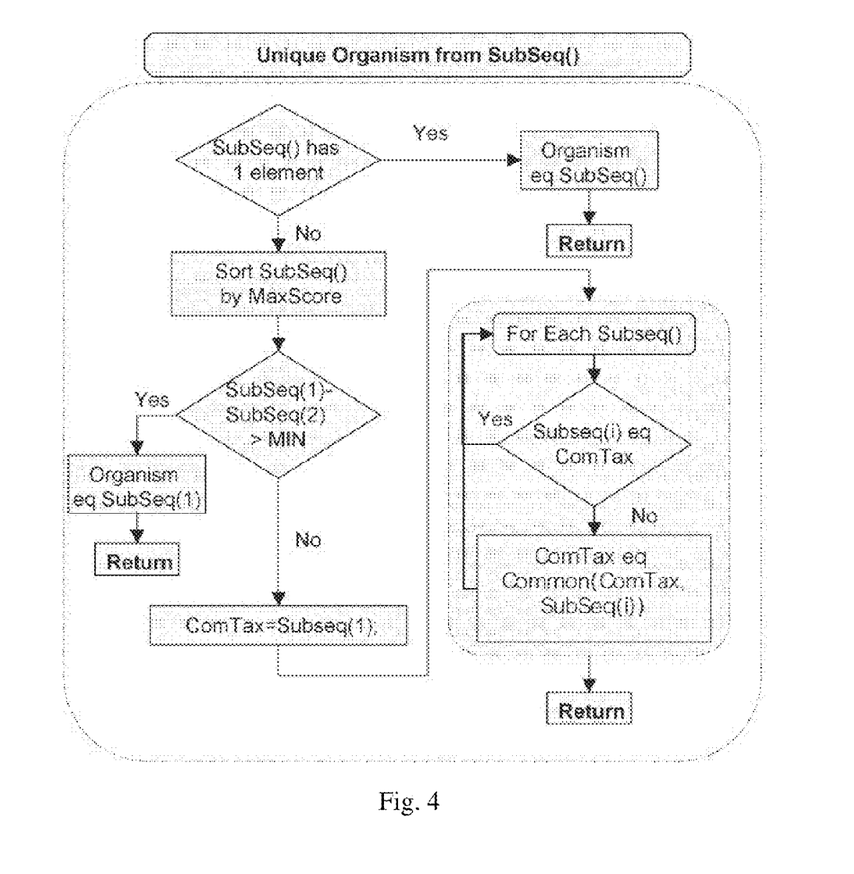
FIG. 4. is a schematic of the subtask of Task 1, which determines the organism, determined for a ProSeq based on the results found for its SubSeq. All of the SubSeq of a particular ProSeq are compared between to determine the two best scoring SubSeq. When there was a single SubSeq or one scored much better than the other, the ProSeq inherited the properties of that SubSeq. Otherwise the common taxonomic class was determined as described in the patent text.

After each SubSeq was examined, the algorithm moved to the next task, which was to determine the identified organism of the ProSeq from the SubSeq (FIG. 4). If all the elements of SubSeq had an identified organism value of Null, then the ProSeq was negative and the next ProSeq was examined. When there was only a single element in SubSeq for a ProSeq or all the elements in SubSeq had the same identified organism, then a Result1 entry was created for the identified organism and its organism uniqueness was either TaxUnique if there were multiple SubSeq entries or it inherited the state of the single SubSeq entry. When there are many entries in SubSeq that had different identified organisms further analysis was performed. The SubSeqs were then re-sorted by MaxScore (bit score) so that elements with the highest two best Scores were SubSeq(1) and SubSeq(2). If SubSeq(1) had a Score that was ≧30% (score ratio threshold) than SubSeq (2)'s Score, then the ProSeq inherited SubSeq(1)'s organism uniqueness and identified organism. Otherwise the ProSeq's organism state was TaxAmbig and the identified organism was the common parent taxonomic class of all the subsequences. If all subsequences were contained in only two taxonomic classes that were direct child and parent, the identified organism was the organism of the subsequences in the child class. The subtask covered in FIG. 4 was completed and the Task I loop continued. A list of ProSeq that had detected organisms was built up in the Result1 array.

Overall Pathogen Identification and Positive Calls

After Task I was completed, Task II (see FIG. 1) was used to examine the identified organism values listed in Result1 and grouped them together if they identified the same taxonomic class. Each entry in Result1 was examined and a new entry was created in Result2 if the identified organism did not appear in this list. In most cases, the entries of Result2 represented the individual organisms that were detected, but might still contain redundant information. Entries in Result2 with identified organisms where one was the taxonomic parent of the other might actually represent the same pathogen. The same identification might not have occurred because the genomic target did not hybridize well to both ProSeq for a variety of possible reasons. Alternatively, two different but closely related organisms might both hybridize to the microarray.

Although it was difficult to relate results from separate ProSeqs to each other, Task III handled the final examination and decisions as currently implemented. The previous tasks were specifically implemented so that information about what a ProSeq was intended to detect was not considered. This allowed these lower cases to be capable of recognizing not just positive and negative but also cases that were indeterminate. In the final task, the algorithm considered whether the ProSeqs identified the organisms that they were designed to detect. Clear negative ProSeqs and ProSeqs that were indeterminate were considered negative for a target pathogen. The grouping of the ProSeqs for this was based upon the grouping already performed in task II. The entries of Result2 were looped over. The ProSeq of an entry was used to look up the pathogen in a table that it was targeted for. If the identified organism of the Result2 entry was the same as or a child of target pathogen taxonomic class, then the Pathogen( ) array was updated with a positive entry for that targeted pathogen. If the Pathogen( ) array was null for that pathogen, the pathogen level identified organism was that of the Result2( ) entry. If an entry was already placed in the pathogen, then further comparison was required. The Result2( ) and Pathogen entries were compared. If they had a direct child parent relationship, the identified organism of the Pathogen was the taxonomic class of the child. Otherwise the common parent taxonomic class was reported as the positively identified organism. In most cases where all the ProSeqs for a pathogen hybridized well, a fine level discrimination was reported. But if one or more ProSeqs hybridized less well, the reported positive target pathogen was only identified at the genus or species level. The results of all 3 tasks were reported so that manual re-examination was possible. Note that organisms identified in Task II that did not belong to target pathogens were reported as a non-target positive return. The details of what was identified in these cases required examination of Task II level results.

Pathogen Identification

*Chlamydia pneumoniae* samples with 10 to 1000 genome copies (via ref. 21 methods) were chosen to illustrate how pathogen detection and identification was done when multiple ProSeq were targeted for the same pathogen (21). RPM v.1 has three highly conserved ProSeqs selected from the genes encoding for the major outer membrane proteins VD2 and VD4, and the DNA-directed RNA polymerase (rpoB) gene. The HybSeqs from the different samples differed only in how many unique base calls as shown in Table 1. The percentage of the ProSeq called varied from 80 to 100% except for one case at a concentration of 10 that had only 11% of the rpoB ProSeq producing unique calls indicating that the detection limits of the assay have been reached is above this concentration. Table 1 listed the determinations made for the SubSeq and at the end of each Task for the various samples. The ProSeq from the different cases produced the same number of SubSeq. These SubSeq from different samples reported different bit scores for the same top ranked returns from BLAST. In fact VD2 and VD4 produced exactly the same results. The NCBI taxonomy database classified the returns into four distinct groups, which represented the C. pneumoniae taxonomic group and three child strain groups. AE001652, AE002167, AE017159, and BA000008 appeared in the returns of all the ProSeq for each sample, since they represented database entries of completely sequenced genomes. One rpoB SubSeq produced for its organism uniqueness, SeqUniqu. All other SubSeq were TaxAmbig as multiple returns from different taxonomic classes were returned. Since the VD2 and VD4 ProSeq each have a single SubSeq, Task I assigned the ProSeq the state of the SubSeq. For the rpoB ProSeq, the bit score of one SubSeq was large enough that the algorithm assigned that SubSeq's identification to the ProSeq. Task II of the algorithm grouped all three ProSeqs together since they all had the same identified organism and TaxAmbig was assigned. The result of task III was positive for target pathogen C. pneumoniae and this decision was straightforward as all the ProSeqs agreed with each other and belonged to the same target pathogen taxonomic class. Although the rpoB ProSeq was SeqUniqu, this was not the final conclusion for Task II as the ProSeq that was SeqUniqu was not the child taxonomic group and other ProSeq were TaxAmbig. The three recognized substrains scored the same, which indicated that the sequence selected for the ProSeqs was very conserved and would not allow discrimination between the strains.

found that the microarray results were in excellent agreement with the conventional sequencing results for clinical samples. The results of running the CIBSI 2.0 program using the updated NCBI database on the raw microarray results were compared to the previous findings (Table 2). The identified organisms were not identical to the original findings due to the difference in database used. In fact, the conventional sequencing results that were submitted to NCBI from that work were found for every sample to be among the returns with the best Score. For 8 of 13 Influenza A and 3 of 12 Influenza B cases, the results of Task I and II found that the conventional sequencing was the single best return and hence the identified organism. Due to the large number of isolate sequences in the database for the hemagglutinin gene it was not surprising that in some cases a single unique entry was not found. In each of the remaining Influenza A samples, the other sequences returned differed by less than 0.2% from the conventional sequence. The fewer samples with unique isolate identifications for Influenza B were due to using an older reference sequence for the ProSeq, which allowed less hybridization to occur (19). This also meant that when multiple sequences were returned for a sample they represented greater genetic variation, up to 2%. This comparison represented only the algorithm analysis at the Task I level for the hemagglutinin (HA) ProSeq, which was the only region conventionally sequenced. There can be no comparison for Task III results, as the previous work did not attempt to obtain a

TABLE 1

Algorithm decisions for C. pneumoniae at several concentrations for SubSeq, Task I, II, and III.

| Genome Copies | ProSeq | Unique calls | # SubSeq | SubSeq organism identification and Uniqueness, Bit score | Task I | Task II | Task III |
|---|---|---|---|---|---|---|---|
| 1000 | VD2 | 89% | 1 | (G1)C. pne, TA, 145 | C. pne, TA | C. pne TA | POSITIVE |
|  | VD4 | 91% | 1 | (G1)C. pne, TA, 145 | C. pne TA |  | C. pne |
|  | rpoB | 80% | 2 | (G2)C. pne, SU, 307 (G3)C. pne, TA, 73 | C. pne SU |  |  |
| 100 | VD2 | 100% | 1 | (G1)C. pne, TA, 164 | C. pne TA | C. pne TA | POSITIVE |
|  | VD4 | 97% | 1 | (G1)C. pne, TA, 156 | C. pne TA |  | C. pne |
|  | rpoB | 80% | 2 | (G2)C. pne, SU, 343 (G3)C. pne, TA, 87 | C. pne SU |  |  |
| 100 | VD2 | 83% | 1 | (G1)C. pne, TA, 136 | C. pne TA | C. pne TA | POSITIVE |
|  | VD4 | 91% | 1 | (G1)C. pne, TA, 145 | C. pne TA |  | C. pne |
|  | rpoB | 84% | 2 | (G2)C. pne, SU, 318 (G3)C. pne, TA, 82 | C. pne SU |  |  |
| 10 | VD2 | 100% | 1 | (G1)C. pne, TA, 164 | C. pne TA | C. pne TA | POSITIVE |
|  | VD4 | 97% | 1 | (G1)C. pne, TA, 156 | C. pne TA |  | C. pne |
|  | rpoB | 90% | 2 | (G2)C. pne, SU, 340 (G3)C. pne, TA, 89 | C. pne SU |  |  |
| 10 | VD2 | 100% | 1 | (G1)C. pne, TA, 164 | C. pne TA | C. pne TA | POSITIVE |
|  | VD4 | 93% | 1 | (G1)C. pne, TA, 148 | C. pne TA |  | C. pne |
|  | rpoB | 11% | 0 | Null, Null | Null, Null |  |  |

(G1) J138 (BA000008), AR39 (AE002167), Tw-183 (AE017159), Cpne (M69230, AF131889, AY555078, M64064, AF131229, AF131230)
(G2) Cpne (S83995)
(G3) J138 (BA000008), AR39 (AE002167), Tw-183 (AE017159)
SU abbreviation for SeqUniqu
TA abbreviation for TaxAmbig Influenza and Human Adenovirus (HAdV) were the only pathogens that had ProSeq selected that would permit detailed strain level discrimination as discussed in previous work (19, 20, 21). This previous work using manual analysis consensus from multiple ProSeq. As a result of the current method of making Task III level identification, the organism reported at this level was less specific (H3N2 or Flu B) for every sample (Supplemental Table 1A and 1B). For HAdV samples, the algorithm also reproduced the finer scale discriminations that had been made previously by manual methods (not shown).

groups A and B sequences were returned with the same score. Regardless of this, the target pathogen positively identified was *M. pneumoniae* for every sample tested.

TABLE 2

Pathogens identified from HA ProSeqs of Influenza A and B Clinical Sample.

| Sample name | Strain identification by previous work (16) | GenBank accession no. | HA3 ProSeq identification by CIBSI 2.0 | GenBank accession no. |
|---|---|---|---|---|
| A/Colorado/360/05 | A/Nepal/1679/2004 (H3N2) | AY945284 | A/Colorado/360/05* | DQ265717 |
| A/Qatar/2039/05 | A/Nepal/1727/2004 (H3N2) | AY945272 | A/Qatar/2039/05 | DQ265707 |
| A/Guam/362/05 | A/Nepal/1679/2004 (H3N2) | AY945264 | A/Guam/362/05 | DQ265715 |
| A/Italy/384/05 | A/Nepal/1727/2004 (H3N2) | AY945272 | A/Italy/384/05 | DQ265713 |
| A/Turkey/2108/05 | A/Nepal/1664/2004 (H3N2) | AY945265 | A/Turkey/2108/05 | DQ265718 |
| A/Korea/298/05 | A/Nepal/1727/2004 (H3N2) | AY945273 | A/Korea/298/05 | DQ265710 |
| A/Japan/1337/05 | A/Malaysia/2256/2004 (H3N2) | ISDN110616 | A/Japan/1337/05* | DQ265712 |
| A/Japan/1383/05 | A/Malaysia/2256/2004 (H3N2) | ISDN110616 | A/Japan/1383/05 | DQ265711 |
| A/Ecuador/1968/04 | A/New York/17/2003 (H3N2) | CY001053 | A/Ecuador/1968/04* | DQ265716 |
| A/Iraq/34/05 | A/Christchurch/178/2004 (H3N2) | ISDN110530 | A/Iraq/34/05 | DQ265714 |
| A/Peru/166/05 | A/Macau/103/2004 (H3N2) | ISDN64772 | A/Peru/166/05 | DQ265708 |
| A/New York/2782/05 | A/New York/391/2005 (H3N2) | CY002056 | A/NewYork/2782/04$* | DQ265709 |
| A/England/400/05 | A/New York/227/2003 (H1N1) | CY002536 | A/England/2005* | DQ265706 |
| B/Peru/1324/04 | B/Milano/66/04 | AJ842082 | B/Peru/1324/04$* | DQ265728 |
| B/Peru/1364/04 | B/Milano/66/04 | AJ842082 | B/Peru/1364/04$* | DQ265726 |
| B/Colorado/2597/04 | B/Texas/3/2002 | AY139049 | B/Colorado/2597/04$* | DQ265724 |
| B/Japan/1905/05 | B/Texas/3/2002 | AY139049 | B/Japan/1905/05$* | DQ265727 |
| B/Japan/1224/05 | B/Texas/3/2002 | AY139049 | B/Japan/1224/05$* | DQ265719 |
| B/Alaska/1777/05 | B/Texas/3/2002 | AY139049 | B/Alaska/1777/05$ | DQ265730 |
| B/England/1716/05 | B/Texas/3/2002 | AY139049 | B/England/1716/05$ | DQ265723 |
| B/England/2054/05 | B/Texas/3/2002 | AY139049 | B/England/2054/05* | DQ265722 |
| B/Hawaii/1990/04 | B/Tehran/80/02 | AJ784042 | B/Hawaii/1990/04 | DQ265721 |
| B/Hawaii/1993/04 | B/Tehran/80/02 | AJ784042 | B/Hawaii/1993/04$* | DQ265720 |
| B/Arizona/148/04 | B/Tehran/80/02 | AJ784042 | B/Arizona/148/04* | DQ265725 |
| B/Arizona/146/04 | B/Tehran/80/02 | AJ784042 | B/Arizona/146/04* | DQ265729 |

*Multiple returns tied with this return
$HybSeq was split into multiple SubSeq

The next example of detection for the *Mycoplasma pneumoniae* pathogen demonstrated a case where there was only a single ProSeq for the target pathogen, which meant that the identified organism for Task I of the algorithm was automatically the result of Task II and was the only ProSeq considered in Task III for this targeted pathogen. This ProSeq was also not optimal for fine discrimination because it was selected from a highly conserved region (345 bp) of the cytadhesin P1 gene. 40 microarrays were tested with the same purified nucleic acid stock and in every case *M. pneumoniae* or its one recognized substrain taxonomic database entries tied for MaxScore. To better understand these returns, the database sequences were examined and subdivided into three groups of sequences, A, B, and C, based on how well they matched the reference sequence used to make the ProSeq. The placement of the database entries into the three groups was determined from a CLUSTAL alignment of the sequences of this gene. This alignment confirmed that the database entries differed significantly more from each other in regions not represented by the ProSeq and contained sufficient variability that would have allowed finer discrimination. Members of Group A exactly matched the ProSeq and could not be distinguished between on the microarray. Similarly, members of group B matched the ProSeq except at the $199^{th}$ position where the base called was C rather than T. Group C sequences contained a few database entries that were more variable and might be distinguished from other entries within the ProSeq. For the 40 experimental tests of *M. pneumoniae*, as much as 95% of the ProSeq hybridized, yet only 65% of the results had an unambiguous base call at the $199^{th}$ position. When it was unambiguous, it always matched group B sequences. In the cases where an N base call was made at the $199^{th}$ location, both These examples showed how decisions were made independent of whether single or multiple ProSeqs were dedicated to a target pathogen. They also illustrated that the level of discrimination possible was strongly determined by the quality of the selected ProSeq. It is possible that for some pathogens fine level discrimination is not required and the currently tested selections on RPM v1 would provide satisfactory information. The CIBSI 2.0 algorithm demonstrated its capability to automatically report the maximum level of discrimination that could be supported by the HybSeq information.

Genetic Near Neighbors

To demonstrate how the algorithm handled closely related genetic species, a sample of a non-targeted pathogen was considered. For Variola major virus, one of the biothreat pathogens on the RPM v.1, the validation runs demonstrated that Variola major virus DNA templates were always positively identified when detected. The array has two ProSeqs from hemagglutinin (VMVHA, ~500 bp) and cytokine response modifier B (VMVcrmB, ~300 bp) genes for Variola major virus detection. Table 3 shows the results for each ProSeq of 18 runs where a close neighbor, Vaccinia virus, was spiked into nasal wash at various concentrations. The percentage of the ProSeq that hybridizes is sufficient that if hybridization patterns were only considered one might assume that this tile is identifying the presence of its target. This would indicate that reference sequence selected was not the best choice. However, when the algorithm was applied none of the samples are in fact identified as Variola major or minor virus. Vaccinia was always one of the Orthopoxvirus species listed with the highest scores for VMVcrmB ProSeq, but in only 7 cases was it uniquely as the probable species detected. In 3 samples with the lowest concentration and fraction of VMVcrmB hybridizing, this ProSeq identified Variola major virus as one among many Orthopoxvirus species that could be the cause of the hybridization. The lower limit of detection for the amplification method used was between this concentration and the one above it. The VMVHA ProSeq made identifications of the Orthopoxvirus species in only two experiments and Variola major virus was listed as one of the tied best scoring returns. In both cases, VMVcrmB ProSeq specifically identified Vaccinia virus as the best match. The percentage of the hybridized ProSeq correlated with concentration of the sample.

TABLE 3

Organism identification from Vaccinia sample on Variola Major virus ProSeqs.

| | ProSeq | | | |
|---|---|---|---|---|
| | VMVCRMB | | VMVHA | |
| CFU | % | identifies | % | identifies |
| $5 * 10^7$ | 77.9 | Vaccinia virus | 29.4 | Orthopoxvirus |
| $5 * 10^7$ | 79.8 | Vaccinia virus | 25.7 | Orthopoxvirus |
| $1.6 * 10^7$ | 79.4 | Vaccinia virus | 14.8 | — |
| $1.6 * 10^7$ | 77.5 | Orthopoxvirus* | 24.5 | — |
| $1.6 * 10^7$ | 76.8 | Vaccinia virus | 21.6 | — |
| $1.6 * 10^7$ | 74.5 | Orthopoxvirus* | 17.3 | — |
| $5 * 10^6$ | 77.9 | Vaccinia virus | 25.7 | — |
| $5 * 10^6$ | 78.3 | Orthopoxvirus* | 22.0 | — |
| $5 * 10^6$ | 73.0 | Vaccinia virus | 13.0 | — |
| $5 * 10^6$ | 73.4 | Orthopoxvirus* | 7.8 | — |
| $1.6 * 10^6$ | 75.3 | Orthopoxvirus* | 8.6 | — |
| $1.6 * 10^6$ | 49.8 | Vaccinia virus | 6.6 | — |
| $1.6 * 10^6$ | 65.5 | Orthopoxvirus* | 10.0 | — |
| $1.6 * 10^6$ | 62.9 | Orthopoxvirus* | 8.2 | — |
| $5 * 10^5$ | 58.4 | Orthopoxvirus* | 9.0 | — |
| $5 * 10^5$ | 56.2 | Orthopoxvirus | 8.0 | — |
| $5 * 10^5$ | 49.0 | Orthopoxvirus | 9.3 | — |
| $5 * 10^5$ | 44.6 | Orthopoxvirus | 7.8 | — |

Figure 5:
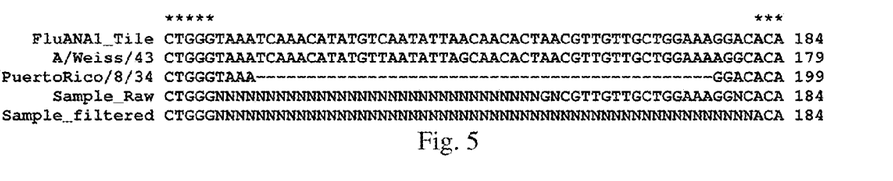
FIG. 5. Alignment of the influenza A NA1 ProSeq (SEQ. ID. NO. 1) and A/Weiss/43 (SEQ. ID. NO. 2), A/PuertoRico/8/34 (SEQ. ID. NO. 3) strains. Raw (SEQ. ID. NO. 4) and filtered (SEQ. ID. NO. 5) hybridization chip results of A/puertoRico/8/34 also shown. * indicate perfectly matched sequences.

*only neighbor species within Orthopoxvirus and not Variola major or Variola minor viruses
CFU—colony forming units Filtering This example demonstrated the importance of the filtering portion of the algorithm by considering the HybSeqs of the ProSeqs for the H1N1 neuraminidase (NA1) and matrix genes from human Influenza A/Puerto Rico/8/34 (H1N1) strain. Filtering was necessary because sending the HybSeq of a ProSeq to BLAST in a single query can bias the scores against strains that have insertions or deletions relative to the ProSeq, especially when using BLAST parameters that maximized the use of base calls. The sliding window test was the portion of the algorithm that controlled filtering. If filtering were turned off, the entire HybSeq would be used in a single subsequence for two influenza ProSeqs that showed significant hybridization. A/Weiss/43 (H1N1) strain was identified as the most likely strain from the HybSeq of the NA1 ProSeq while the HybSeq of the matrix ProSeq correctly identified A/Puerto Rico/8/34. To better understand the source of biasing, CLUSTAL alignment of the NA1 gene of the two strains and the reference sequence used to make the ProSeq are shown in FIG. 5. The two strains showed 95% identity (67 mismatches in 1362 aligned bases); however, there was a stretch of 45 bases inserted in both A/Weiss/43 (SEQ ID NO. 2) and the NA1 ProSeq (SEQ ID NO. 1) compared to A/Puerto Rico/8/34 (SEQ ID NO. 3). With the default filtering on, the NA1 ProSeq was split into five SubSeqs as the algorithm encountered large stretches of no calls. In Task I, the algorithm determined that three of the SubSeqs, which were shorter, had an identified organism of H1N1 as several isolates including A/Puerto Rico/8/34 tied with the best score, while the two other SubSeqs had an identified organism of only the A/Puerto Rico/8/34 strain as being the closest match. The organism identified by the NA1 ProSeq was A/Puerto Rico/8/34 because one of the SubSeqs had a much higher score. This ProSeq supported the same strain identification made in the matrix ProSeq. The organism identified was A/Puerto Rico/8/34 because two ProSeqs detected only that organism. The correct target pathogen was detected with filtering while without filtering the target pathogen level of identification would have been Influenza A (H1N1 subtype) because two organisms were detected, A/Puerto Rico/8/34 and A/Weiss/43. Splitting the HybSeq into SubSeqs to remove biasing may reduce the level of identification as occurred for the three of the five SubSeqs in this case. The previous example for Vaccinia was another instance where the wrong species (*Camel pox* or *Callithrix jacchus*) identification would occur if the filtering was not used. Clinical samples in Table 2 showed that HybSeqs split into multiple SubSeqs were capable of very specific identification.

As a minor point, when multiplex strategies rather than generic were used for amplification, it was necessary to perform additional filtering to remove potential biasing from the specific primers as described in the methods. FIG. 5 has the raw (SEQ ID NO. 4) and mask filtered (SEQ ID NO. 5) results for the hybridization of A/Puerto Rico/8/34 to show an example of this interference. There is in addition to the problem with biasing for the reasons described before a sequence of 18 bases present in the raw result that after filtering have been made N since they are in a location that interacts with the primers. If these base calls were included in the subsequences constructed, the query for the ProSeq would favor an incorrect strain.

The algorithm successfully provided pathogen identification to the maximum level of detail possible (species or strain) depending on the quality of each ProSeq. This identification capability requires minimal input on the identity of the pathogens making non-expert use feasible. The crucial feature incorporated that allowed complete automation was the use of taxonomic databases, which classify organisms into ordered groups and provide relationships between organism entries, allowing removal of redundancies, comparison of different related prototype sequences, and simplification of data presentation. This allows databases, i.e. NCBI, that are redundant and subject to minimal curation but which constantly receive updated and new sequence information to be used with great success. Although this has been demonstrated using only the NCBI databases, other databases or custom made ones could have easily been used, which might improve performance. The algorithm is capable of providing accurate identifications at all analysis levels for pathogens that are less variable or are represented by highly conserved ProSeqs. For more variable or rapidly mutating pathogens, e.g. Influenza A virus, Tasks I and II still provided accurate detailed identifications, but Task III was unable to report fine scale discrimination. The comparison of the conventionally sequenced Influenza virus gene sequences illustrated that the algorithm is capable of automatically adjusting for updates in databases. The algorithm demonstrated its capability to properly distinguish hybridizations on a ProSeq caused by the specified pathogen from those caused by genetically close (near neighbor) strains and did not make incorrect identifications, eliminating one potential cause of false positives. Filtering the raw hybridization results served to reduce the computation time, accounted for potential primer interference, and more importantly reduced potential biasing. This simple integrated algorithm provided sufficient and accurate identification, so that immediate use of the RPM v.1 or similar resequencing arrays and assay is possible.

Besides demonstrating the success of the CIBSI 2.0 program, the work involved in developing the algorithm allowed insight into the importance of proper ProSeq selection. The RPM v.1 was the first resequencing array designed specifically for multiple pathogen detection using database similarity searching and served as a prototype for this application. It has been demonstrated that a single ProSeq with as few as 100 bp, when designed correctly, can be sufficient to unambiguously identify an organism. However, it is clearly indicated that several longer ProSeqs provide better confirmation and more detailed information of a pathogen. The emphasis of the design to this point has been on capabilities that are generally applicable to any pathogen. Improving on performance of Task III may require more information about an individual pathogen and may have to be developed for each specific pathogen or class of pathogens. This information also may be required for the algorithm to identify which differences between a sample and database entries represent significant mutations. The hierarchal design of the data analysis can make it easy to incorporate analysis that build upon the analysis already performed. The use of properly designed resequencing microarrays and this automated detection algorithm can provide a way forward to developing assays that can test for multiple organisms simultaneously while providing fine strain level discrimination giving access to information about detailed strain recognition, antibiotic resistance markers and pathogenicity. This will allow the analysis of partial sequence information from multiple organisms for applications such as differential diagnostics for illnesses with multiple potential causes (i.e. febrile respiratory illness), tracking of emergent pathogens, distinction of biological threats from harmless near genetic neighbors in surveillance applications, and for tracking the impact of co-infections or super infections. The concept of categorizing and reporting different degrees of identification depending on the quality of samples and set of target sequences is not limited to resequencing microarrays but is more generally applicable to any platform that is capable of returning sequence level calls that can be used to query a reference DNA database. As the trend for assays that test for multiple pathogens increases, automated analysis tools, such as this one, become more crucial for rapid identification in simple formats useful to the non-expert on a day to day basis.

Source Code

The computer program listing appendix contains a PERL source code listing of an embodiment of the disclosed methods. The "overclinical" program is the top-level program that runs the other program. "fstorepi" performs the filtering, subsequence preparation, and query file preparation. This program uses in input file "primerhyb.dat" containing the predetermined list of positions to be changed to N. "runblast" performs the BLAST query. "dbparse" performs the taxonomic analysis. This program uses an input file "chip1pathogengroups" containing a list of target pathogens for each ProSeq.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

REFERENCES

1. Whelen, A. C. and Persing, D. H. (1996) The role of nucleic acid amplification and detection in the clinical microbiology laboratory. *Annu Rev Microbiol*, 50, 349-373.
2. McDonough, E. A., Barrozo, C. P., Russell, K. L. and Metzgar, D. (2005) A multiplex PCR for detection of *Mycoplasma pneumoniae, Chlamydophila pneumoniae, Legionella pneumophila*, and *Bordetella pertussis* in clinical specimens. *Mol Cell Probes*, 19, 314-322.
3. Roth, S. B., Jalava, J., Ruuskanen, O., Ruohola, A. and Nikkari, S. (2004) Use of an oligonucleotide array for laboratory diagnosis of bacteria responsible for acute upper respiratory infections. *J Clin Microbiol*, 42, 4268-4274.
4. Gardner, S. N., Kuczmarski, T. A., Vitalis, E. A. and Slezak, T. R. (2003) Limitations of TaqMan PCR for detecting divergent viral pathogens illustrated by hepatitis A, B, C, and E viruses and human immunodeficiency virus. *J Clin Microbiol*, 41, 2417-2427.
5. Ecker, D. J., Sampath, R., Blyn, L. B., Eshoo, M. W., Ivy, C., Ecker, J. A., Libby, B., Samant, V., Sannes-Lowery, K. A., Melton, R. E. et al. (2005) Rapid identification and strain-typing of respiratory pathogens for epidemic surveillance. *Proc Natl Acad Sci USA*, 102, 8012-8017.
6. Zammatteo, N., Hamels, S., De Longueville, F., Alexandre, I., Gala, J. L., Brasseur, F. and Remade, J. (2002) New chips for molecular biology and diagnostics. *Biotechnol Annu Rev*, 8, 85-101.
7. Campbell, C. J. and Ghazal, P. (2004) Molecular signatures for diagnosis of infection: application of microarray technology. *J Appl Microbiol*, 96, 18-23.
8. Briese, T., Palacios, G., Kokoris, M., Jabado, O., Liu, Z., Renwick, N., Kapoor, V., Casas, I., Pozo, F., Limberger, R. et al. (2005) Diagnostic system for rapid and sensitive differential detection of pathogens. *Emerg Infect Dis*, 11, 310-313.
9. Hacia, J. G. (1999) Resequencing and mutational analysis using oligonucleotide microarrays. *Nat Genet*, 21, 42-47.
10. Kozal, M. J., Shah, N., Shen, N., Yang, R., Fucini, R., Merigan, T. C., Richman, D. D., Morris, D., Hubbell, E., Chee, M. et al. (1996) Extensive polymorphisms observed in HIV-1 clade B protease gene using high-density oligonucleotide arrays. *Nat Med*, 2, 753-759.
11. Cutler, D. J., Zwick, M. E., Carrasquillo, M. M., Yohn, C. T., Tobin, K. P., Kashuk, C., Mathews, D. J., Shah, N. A., Eichler, E. E., Warrington, J. A. et al. (2001) High-throughput variation detection and genotyping using microarrays. *Genome Res*, 11, 1913-1925.
12. Gingeras, T. R., Ghandour, G., Wang, E., Berno, A., Small, P. M., Drobniewski, F., Alland, D., Desmond, E., Holodniy, M. and Drenkow, J. (1998) Simultaneous genotyping and species identification using hybridization pattern recognition analysis of generic Mycobacterium DNA arrays. *Genome Res*, 8, 435-448.
13. Lin, B., Vahey, M. T., Thach, D., Stenger, D. A. and Pancrazio, J. J. (2003) Biological threat detection via host gene expression profiling. *Clin Chem*, 49, 1045-1049.
14. Wilson, W. J., Strout, C. L., DeSantis, T. Z., Stilwell, J. L., Carrano, A. V. and Andersen, G. L. (2002) Sequence-specific identification of 18 pathogenic microorganisms using microarray technology. *Mol Cell Probes*, 16, 119-127.
15. Wilson, K. H., Wilson, W. J., Radosevich, J. L., DeSantis, T. Z., Viswanathan, V. S., Kuczmarski, T. A. and Andersen, G. L. (2002) High-density microarray of small-subunit ribosomal DNA probes. *Appl Environ Microbiol*, 68, 2535-2541.

16. Zwick, M. E., McAfee, F., Cutler, D. J., Read, T. D., Ravel, J., Bowman, G. R., Galloway, D. R. and Mateczun, A. (2005) Microarray-based resequencing of multiple *Bacillus anthracis* isolates. *Genome Biol,* 6, R10.
17. Wong, C. W., Albert, T. J., Vega, V. B., Norton, J. E., Cutler, D. J., Richmond, T. A., Stanton, L. W., Liu, E. T. and Miller, L. D. (2004) Tracking the evolution of the SARS coronavirus using high-throughput, high-density resequencing arrays. *Genome Res,* 14, 398-405.
18. Sulaiman, I. M., Liu, X., Frace, M., Sulaiman, N., Olsen-Rasmussen, M., Neuhaus, E., Rota, P. A. and Wohlhueter, R. M. (2006) Evaluation of affymetrix severe acute respiratory syndrome resequencing GeneChips in characterization of the genomes of two strains of coronavirus infecting humans. *Appl Environ Microbiol,* 72, 207-211.
19. Wang, Z., Daum, L. T., Vora, G. J., Metzgar, D., Walter, E. A., Canas, L. C., Malanoski, A. P., Lin, B. and Stenger, D. A. (2006) Identifying Influenza Viruses with Resequencing Microarrays. *Emerg Infect Dis,* 12, 638-646.
20. Lin, B., Wang, Z., Vora, G. J., Thornton, J. A., Schnur, J. M., Thach, D. C., Blaney, K. M., Ligler, A. G., Malanoski, A. P., Santiago, J. et al. (2006) Broad-spectrum respiratory tract pathogen identification using resequencing DNA microarrays. *Genome Res.* 16:527-535
21. Lin, B., Blaney, K. M., Malanoski, A. P., Ligler, A. G., Schnur, J. M., Metzgar, D., Russell, K. L. and Stenger, D. A. (2006). Naval Research Laboratory.
22. Altschul, S. F., Gish, W., Miller, W., Myers, E. W. and Lipman, D. J. (1990) Basic local alignment search tool. *J Mol Biol,* 215, 403-410.
23. Davignon, L., Walter, E. A., Mueller, K. M., Barrozo, C. P., Stenger, D. A. and Lin, B. (2005) Use of resequencing oligonucleotide microarrays for identification of *Streptococcus* pyogenes and associated antibiotic resistance determinants. *J Clin Microbiol,* 43, 5690-5695.

What is claimed is:

1. A method comprising:
submitting a plurality of pathogen biological sequences in queries to a taxonomic database to produce a plurality of taxonomic results;
  wherein the pathogen biological sequences are the output of genetic database queries that return a score for each sequence;
determining whether the taxonomic results contain only a single taxon;
determining whether the highest score among the plurality of pathogen biological sequences exceeds the score of the pathogen biological sequence having the second highest score by a predetermined score ratio threshold;

determining whether all the taxonomic results contain only a child taxon and a direct parent taxon to the child taxon; and reporting a taxonomic identification based on the taxonomic results;

wherein reporting the taxonomic identification uses one of the following criteria-based steps, the choice of step being the first step wherein the criterion is satisfied:

reporting the single taxon when the taxonomic results contain only the single taxon;

reporting the taxonomic result of the pathogen biological sequence having the highest score among the plurality of sequences when the highest score exceeds the score of the pathogen biological sequence having the second highest score by the predetermined score ratio threshold;

reporting the child taxon when all the taxonomic results contain only the child taxon and the direct parent taxon to the child taxon; and reporting a common parent taxon in all other cases; and wherein the method is performed using a suitably programmed computer.

2. The method of claim 1, wherein the score ratio threshold is about 30%.

3. A method comprising:

performing the method of claim 1 two or more times with different pluralities of pathogen biological sequences to generate a plurality of taxonomic identifications;

wherein the inputs to the genetic database queries are subsequences that are correlated to predetermined prototype sequences from target pathogens; and grouping identical taxonomic identifications with the corresponding prototype sequences.

4. The method of claim 3, further comprising:

reporting a positive result for each of the target pathogens for which one of the taxonomic identifications that corresponds to one of the prototype sequences of the target pathogen is the same as or a child taxon of the target pathogen taxon.

5. The method of claim 4, further comprising:

reporting a final taxonomic identification of:

a single taxon when the positive results contain only the single taxon;

a child taxon when all the positive results contain only the child taxon and a direct parent taxon to the child taxon; or a common parent taxon in all other cases.

* * * * *

SEQUENCE LISTING

```
<160> NUMBER OF SEQ ID NOS: 5

<210> SEQ ID NO 1
<211> LENGTH: 61
<212> TYPE: DNA
<213> ORGANISM: Human Influenza A
<220> FEATURE:
<221> NAME/KEY: gene
<222> LOCATION: (1)..(61)
<223> OTHER INFORMATION: NA1

<400> SEQUENCE: 1
ctgggtaaat caaacatatg tcaatattaa caacactaac gttgttgctg gaaaggacac      60
a                                                                     61

<210> SEQ ID NO 2
<211> LENGTH: 61
<212> TYPE: DNA
<213> ORGANISM: Human Influenza A
<220> FEATURE:
<221> NAME/KEY: gene
<222> LOCATION: (1)..(61)
<223> OTHER INFORMATION: NA1

<400> SEQUENCE: 2
ctgggtaaat caaacatatg ttaatattag caacactaac gttgttgctg gaaaaggcac      60
a                                                                     61

<210> SEQ ID NO 3
<211> LENGTH: 16
<212> TYPE: DNA
<213> ORGANISM: Human Influenza A
<220> FEATURE:
<221> NAME/KEY: gene
<222> LOCATION: (1)..(16)
<223> OTHER INFORMATION: NA1

<400> SEQUENCE: 3
ctgggtaaag gacaca                                                     16

<210> SEQ ID NO 4
<211> LENGTH: 61
<212> TYPE: DNA
<213> ORGANISM: A/Puerto Rico/8/34
<220> FEATURE:
<223> OTHER INFORMATION: Raw data
```

```
<220> FEATURE:
<221> NAME/KEY: misc_feature
<222> LOCATION: (1)..(61)
<223> OTHER INFORMATION: n is a, c, g, or t

<400> SEQUENCE: 4
ctgggnnnnn nnnnnnnnnn nnnnnnnnnn nnnnnnngnc gttgttgctg gaaaggncac    60
a                                                                    61

<210> SEQ ID NO 5
<211> LENGTH: 61
<212> TYPE: DNA
<213> ORGANISM: A/Puerto Rico/8/34
<220> FEATURE:
<223> OTHER INFORMATION: Filtered data
<220> FEATURE:
<221> NAME/KEY: misc_feature
<222> LOCATION: (1)..(61)
<223> OTHER INFORMATION: n is a, c, g, or t

<400> SEQUENCE: 5
ctgggnnnnn nnnnnnnnnn nnnnnnnnnn nnnnnnnnnn nnnnnnnnnn nnnnnnnnac    60
a                                                                    61
```